(12) United States Patent
Ho et al.

(10) Patent No.: US 8,251,066 B1
(45) Date of Patent: Aug. 28, 2012

(54) EXHALATION PORT WITH BUILT-IN ENTRAINMENT VALVE

(75) Inventors: Peter Chi Fai Ho, Pittsburgh, PA (US); James DiPasquale, Allison Park, PA (US); Elias G. Diacopoulos, Export, PA (US)

(73) Assignee: Ric Investments, LLC, Wilmington, DE (US)

( * ) Notice: Subject to any disclaimer, the term of this patent is extended or adjusted under 35 U.S.C. 154(b) by 1056 days.

(21) Appl. No.: 11/312,027

(22) Filed: Dec. 20, 2005

Related U.S. Application Data (60) Provisional application No. 60/638,678, filed on Dec. 22, 2004.

(51) Int. Cl.
  *A61M 16/06* (2006.01)
  *A62B 18/10* (2006.01)
  *F16K 15/00* (2006.01)
  *F16K 17/00* (2006.01)

(52) U.S. Cl. ......... 128/207.12; 128/204.18; 128/205.24; 128/205.25; 128/206.15; 128/207.16; 251/89.5; 137/513.3; 137/513.5

(58) Field of Classification Search ............ 128/207.12, 128/207.16, 204.29, 205.24, 204.18; 251/89.5; 137/513.5, 513.3
See application file for complete search history.

(56) References Cited

U.S. PATENT DOCUMENTS

| | | | | |
|---|---|---|---|---|
| 672,384 A * | 4/1901 | Marvin | | 184/52 |
| 879,029 A * | 2/1908 | Blackburn | | 138/46 |
| 3,520,330 A * | 7/1970 | Szwargulski | | 137/613 |
| 3,593,343 A * | 7/1971 | Viggers | | 623/2.35 |
| 3,727,635 A * | 4/1973 | Todd | | 137/513.5 |
| 3,841,349 A * | 10/1974 | Todd | | 137/513.5 |
| 3,850,171 A * | 11/1974 | Ball et al. | | 128/204.25 |
| 3,901,475 A * | 8/1975 | Dreibelbis | | 251/360 |
| 3,908,987 A * | 9/1975 | Boehringer | | 482/13 |
| 4,030,520 A * | 6/1977 | Sands | | 137/513.5 |
| 4,535,800 A * | 8/1985 | Leech | | 137/205 |
| 4,655,213 A * | 4/1987 | Rapoport et al. | | 128/205.25 |
| 4,951,701 A * | 8/1990 | Boehmer | | 137/199 |
| 5,018,517 A * | 5/1991 | Liardet | | 128/200.24 |
| 5,438,981 A | 8/1995 | Starr et al. | | |
| 5,560,354 A * | 10/1996 | Berthon-Jones et al. | | 128/205.25 |
| 5,647,355 A | 7/1997 | Starr et al. | | |
| 5,839,436 A * | 11/1998 | Fangrow et al. | | 128/205.24 |
| 5,878,743 A | 3/1999 | Zdrojkowski et al. | | |
| 5,906,203 A * | 5/1999 | Klockseth et al. | | 128/205.24 |
| 5,950,623 A * | 9/1999 | Michell | | 128/205.24 |
| 6,032,664 A * | 3/2000 | Gray et al. | | 128/201.27 |
| 6,189,532 B1 | 2/2001 | Hely et al. | | |
| 6,467,483 B1 * | 10/2002 | Kopacko et al. | | 128/207.12 |

(Continued)

*Primary Examiner* — Clinton T Ostrup

(74) *Attorney, Agent, or Firm* — Michael W. Haas (57) ABSTRACT

A pressure sensitive valve device for use with respiratory equipment of the type that produces a pressurized flow of breathing gas. The valve device combines the exhalation and entrainment functions in one valve with a single air path. The valve device provides an exhaust valve function during normal operation and provides a less restricted access to the ambient atmosphere in the event of respiratory equipment malfunction. The valve device includes a valve element that moves between at least two positions. During normal operation, when the pressure generating system is generating a flow of gas, the valve element is in a "closed" or "exhaust valve" position. When in the exhaust valve position, the gas flow to the atmosphere is restricted without being completely blocked off. When the flow of gas is decreased or interrupted, the valve element moves to the "entrainment valve" or "open" position that allows a greater, i.e., less restricted flow, of gas between the user and the ambient atmosphere.

25 Claims, 11 Drawing Sheets

U.S. PATENT DOCUMENTS

| | | | |
|---|---|---|---|
| 6,581,594 B1 * | 6/2003 | Drew et al. | 128/204.18 |
| 6,584,977 B1 | 7/2003 | Serowski | |
| 6,659,102 B1 * | 12/2003 | Sico | 128/206.15 |
| 6,766,800 B2 * | 7/2004 | Chu et al. | 128/205.24 |
| 6,805,123 B2 * | 10/2004 | Seo | 128/206.12 |
| 6,823,865 B2 * | 11/2004 | Drew et al. | 128/204.18 |
| 6,851,425 B2 | 2/2005 | Jaffre et al. | |
| 7,159,587 B2 * | 1/2007 | Drew et al. | 128/204.18 |
| 7,325,572 B2 * | 2/2008 | Schinazi et al. | 138/43 |
| 7,364,571 B2 * | 4/2008 | Schinazi et al. | 604/246 |
| 7,608,061 B2 * | 10/2009 | Schinazi et al. | 604/246 |
| 2001/0004894 A1 * | 6/2001 | Bourdon | 128/204.23 |
| 2002/0157674 A1 * | 10/2002 | Shikani et al. | 128/207.29 |
| 2004/0040563 A1 * | 3/2004 | Chu et al. | 128/206.21 |
| 2004/0094157 A1 * | 5/2004 | Dantanarayana et al. | 128/206.21 |

* cited by examiner

EXHALATION PORT WITH BUILT-IN ENTRAINMENT VALVE

CROSS-REFERENCE TO RELATED APPLICATIONS

This application claims priority under 35 U.S.C. §119(e) from provisional U.S. patent application No. 60/638,678, filed Dec. 22, 2004, the contents of which are incorporated herein by reference.

BACKGROUND OF THE INVENTION

1. Field of the Invention

The present invention relates to an apparatus adapted for use with respiratory equipment and, more particularly, to an exhalation port device with a built-in entrainment valve feature.

2. Description of the Related Art

Pressure support systems that provide a flow of gas to an airway of a patient at an elevated pressure via a patient circuit to treat a medical disorder are well known. For example, it is known to use positive airway pressure devices, such as a continuous positive airway pressure (CPAP) device, to supply a constant positive pressure to the airway of a patient to treat obstructive sleep apnea (OSA) as well as other disorders. It is also known to provide a positive pressure therapy in which the pressure of gas delivered to the patient varies with the patient's breathing cycle or varies with the patient's effort to increase the comfort to the patient. This mode of pressure support is typically referred to as bi-level pressure support. Still other pressure support systems, referred to as auto-titration systems, vary the pressure delivered to the patient based on the monitored condition of the patient, such as whether the patient is snoring, having apneas, etc.

A typical pressure support system comprises a gas flow/pressure generating device that produces a flow of gas and a conduit having a first end portion that is coupled to the outlet of the pressure generating device. The conduit, which is typically referred to as a patient circuit, carries the flow of gas from the pressure generating device during operation of the system. A patient interface, which is typically a nasal or nasal/oral mask, is coupled to a second end portion of the conduit. In a single-limb system, an exhaust vent is provided on the patient interface or the patient circuit to exhaust gas from the patient circuit. A typical exhaust vent is a continuously open port provided in the conduit or patient interface to allow gas to escape from the system to the ambient atmosphere.

Should the gas flow/pressure generating device become dysfunctional, for example as a result of a power outage or other problem, a flow of gas will no longer be delivered to the patient interface. While the conventional exhaust port may provide some fresh gas to the patient, the amount of gas it can provide is typically not adequate to sufficiently ventilate the patient, which may lead to the patient rebreathing their own carbon dioxide.

To address this situation, it is known to provide a valve, typically referred to as an entrainment valve, at or near the patient interface. The entrainment valve functions by providing automatic access of the patient's airway to the ambient atmosphere if the pressure or flow in the gas flow delivery system falls below a threshold level. More specifically, a typical entrainment valve is provided at the inlet of the patient interface and includes a relatively large port that is selectively blocked by a movable element. The moveable element blocks the large port during normal operation because the gas flow or pressure holds the moveable element in place over the large port. If the flow or pressure falls, for example, during a power outage or equipment malfunction, the moveable element is no longer held over the large port, thereby unblocking it and allowing the patient automatic access to the ambient atmosphere through the large port so that he or she receives adequate ventilation. Examples of such entrainment valve are disclosed in U.S. Pat. Nos. 5,438,981 and 5,647,355 both to Starr et al. and in U.S. Pat. No. 6,851,425 to Jaffre et al.

It can be appreciated that these conventional entrainment valve systems require one valve system to provide the entrainment valve function in the event of a pressure loss and a separate valve system to provide the continuous exhaust gas flow function during normal operation. The need for separate components, with separate exhaust paths, complicates the patient circuit and patient interface system, increasing its cost and complexity, and does not efficiently use the space available near the patient.

SUMMARY OF THE INVENTION

Accordingly, it is an object of the present invention to provide a valve system for gas flow delivery system that overcomes the shortcomings of conventional valve systems. This object is achieved according to one embodiment of the present invention by providing a valve device for use in a system for delivering a flow of gas to an airway of a patient, where the valve device includes, a valve body having an outlet open to ambient atmosphere and a valve element operatively coupled to the valve body such that valve element is moveable between at least two positions.

When the valve element is in a first position, the exhaust gas flow between the valve device and an ambient atmosphere is at first level of restriction. When in a second position, the exhaust gas flow is at a second level of restriction that is greater than the first level of restriction. The valve element is disposed in the first position when the flow of gas has an insufficient pressure or rate of flow to overcome a biasing force acting on the valve element. Conversely, the valve element is disposed in the second position when the flow of gas has a sufficient pressure or rate to overcome the biasing force acting on the valve element. In this manner the valve element provides the function of an entrainment valve, i.e., automatically providing the user with access to the ambient atmosphere when system is impaired or malfunctions, when in the first position, and provides the function of a conventional exhaust port when in the second position.

A valve structure is provided to prevent the valve element from completely blocking the exhaust gas flow when in the second position. This feature of the present invention allows the valve element, in cooperation with the valve body, to provide the continuous exhaust gas flow from the system during normal use of the pressure support system.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the

DETAILED DESCRIPTION OF THE EXEMPLARY EMBODIMENTS

Figure 1:
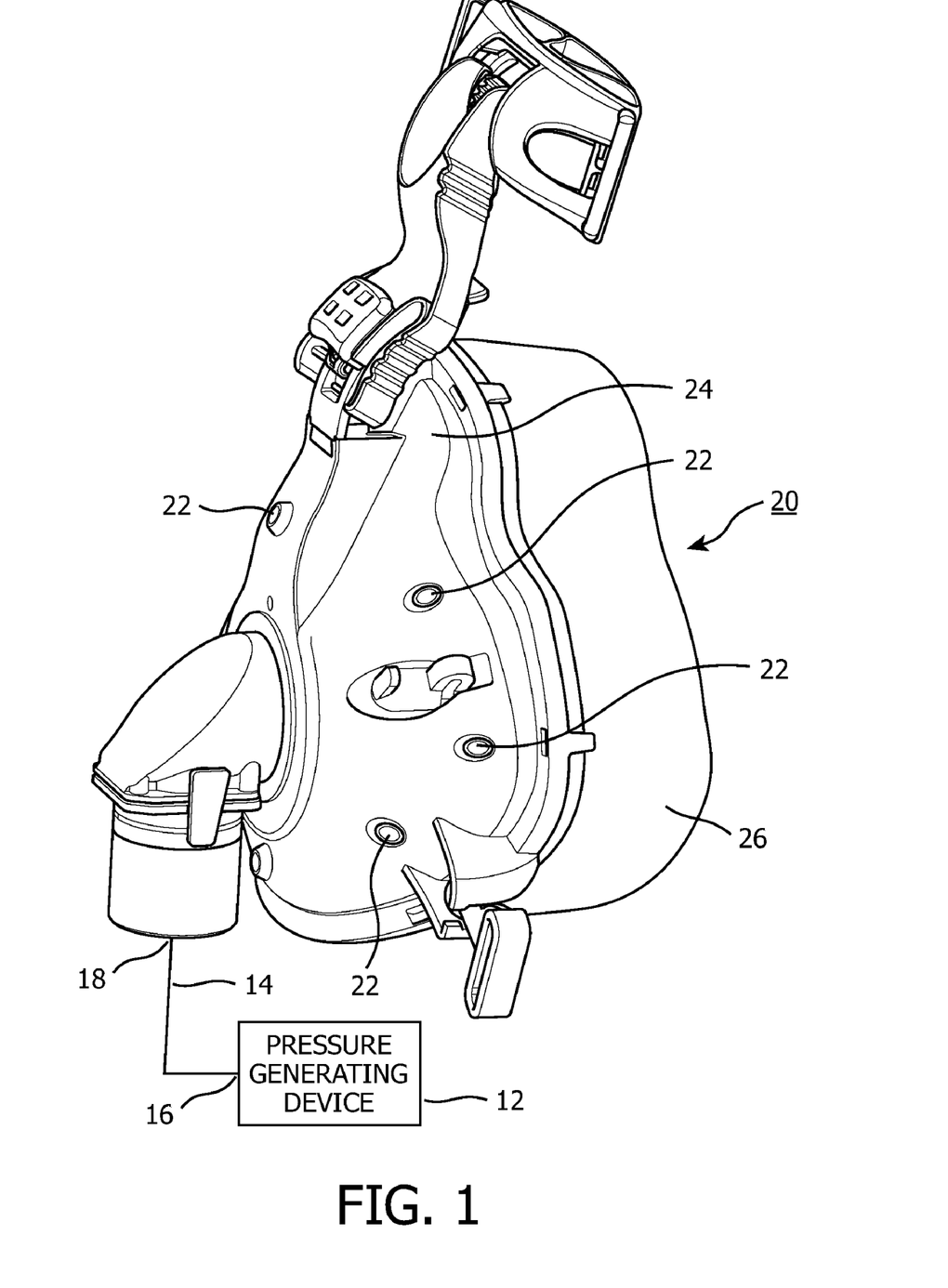
FIGS. 1 and 2 are side and front perspective views, respectively, of a patient interface according to the principles of the present invention.
Figure 2:
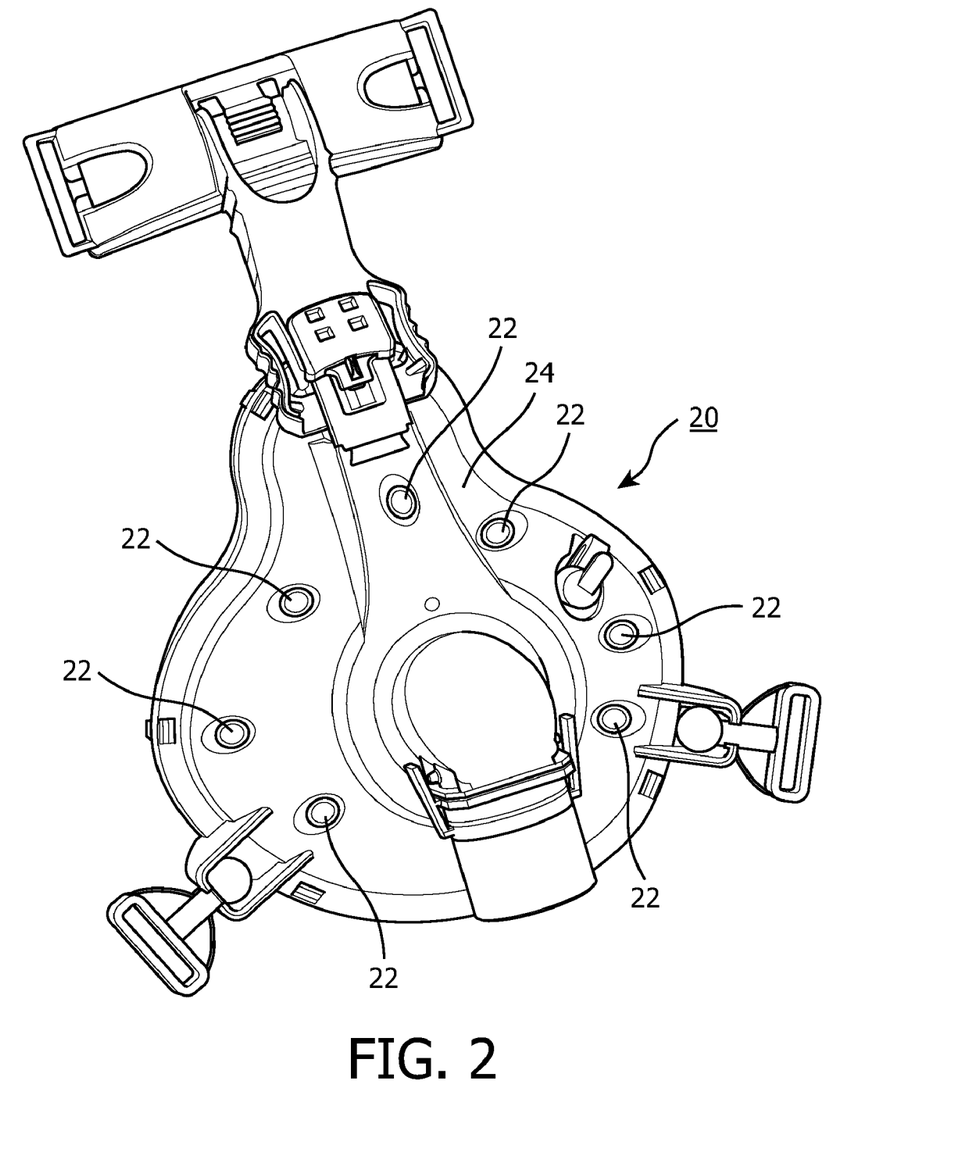

Referring first to FIGS. 1-2, a system for delivering a flow of breathing gas to a patient is illustrated. The system comprises a pressure/flow generating device 12 that produces a flow of gas and a delivery conduit (patient circuit) 14 having a first end portion 16 operatively coupled to the pressure generating device 12 and a second end portion 18. Patient circuit 14 carries the flow of gas from pressure/flow generating device 12 during operation of the system to a patient interface 20 coupled to second end portion 18.

A valve device 22, according to at least one embodiment of the present invention, is provided on the patient interface. Valve device 22 of the present invention is shown in use with a positive airway pressure system. It is to be understood that the valve device can used with any type of gas delivery/pressure generating system, including, but not limited to a ventilator, CPAP devices, bi-level devices, auto-titration devices, and any combination thereof. The valve device can also be used with pressure/flow delivery systems used outside the medical field.

In the illustrated embodiment, patient interface 20 includes a faceplate 24 and a cushion or seal 26 for contacting the surface of a patient. In the illustrated embodiment, patient interface 20 is a full face mask, meaning that it covers the user's nose and mouth. It is to be understood, however, that patient interface 20 may be any interface device, such as a nasal mask that covers the patient's nose, or a nasal cannula type of mask. It is to be further understood that the patient interface can include a variety of other features, such as multiple-flap cushions, headgear connectors, moveable supports (such as the forehead support shown in FIGS. 1 and 2), supplemental oxygen ports, and any other feature associated with patient interface devices.

Figure 3:
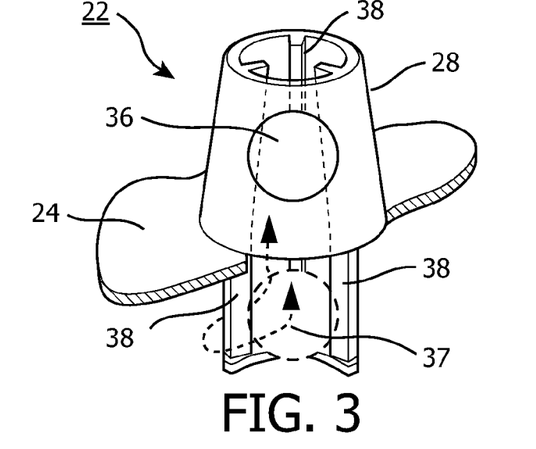
FIG. 3 is a partial sectional view of a first embodiment for a valve device provided in the patient interface according to the principles of the present invention.
Figure 4:
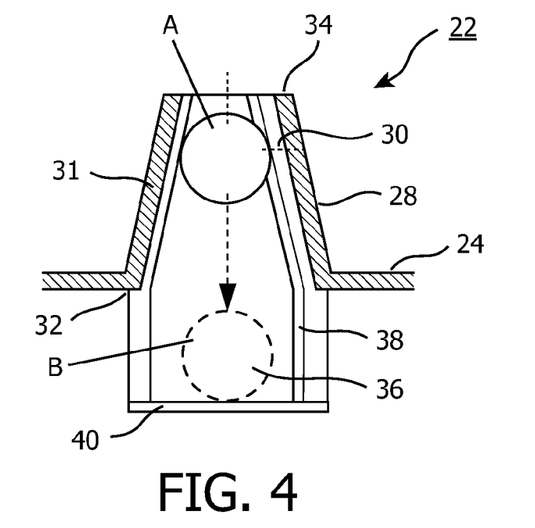
FIGS. 4 and 5 are a sectional side and top views, respectively, of the valve device of FIG. 3.
Figure 5:
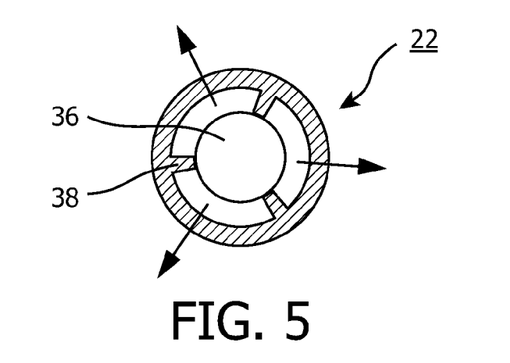

FIGS. 3-5 illustrate in greater detail a first embodiment of valve device 22 according to the principles of the present invention. In this illustrated embodiment, valve device 22 is incorporated into patient interface 20. Specifically, valve device 22 is integral with faceplate 24. The position of valve device 22 on the patient interface illustrated in FIGS. 1-2 is just one example according to the present invention. It is to be understood that the valve device or devices could be located at other positions, such as on the patient circuit, the coupling between the patient circuit and the faceplate, the seal, or any combination thereof.

In this exemplary embodiment, valve device 22 comprises a frusta-conical shaped valve body 28 extending outwardly from the patient interface faceplate 24 (away from the patient in use). Valve body 28 further includes a frusta-conical shaped interior chamber 30 having an interior sidewall 31. Interior chamber 30 includes an inlet 32 at faceplate 24 and an outlet 34 at end of valve body 28 distal from the faceplate. The diameter of outlet 34 is smaller than the diameter of inlet 32.

A valve element, which in this embodiment is a ball 36 with a smooth surface, freely floats within interior chamber 30. Ball 36 can be made from any suitable material, such as an elastomer, rigid plastic, metal, or glass. At least one interior rib 38 is provided on interior sidewall 31 of the interior chamber 30. Ribs 38 extend from outlet 34 of the interior chamber 30 along sidewall 31 to a position below valve body 28 and within the interior of the patient interface. In the illustrate embodiment, three ribs are provided at an even spacing around the perimeter of the valve body 28. However, the present invention contemplates that more or less ribs can be used.

A retaining member 40 is connected to the ends of ribs 38 to prevent ball 36 from escaping from the valve device into the chamber defined in the patient interface. The ends of ribs 38 extend into the patient interface a distance greater than the diameter of ball 36 so that a gap exists between the ball and the valve plate when the ball is resting on retaining member 40. Ribs 38 and retaining member 40 form a retaining seat. The diameter of outlet 34 of interior chamber 30, including the ribs 38, prevents the ball from escaping from outlet 34. The ribs form a valve structure that prevents the valve element, i.e., the ball, from completely blocking the valve device, i.e., from completely restricting the flow of gas from an interior of the patient interface to the ambient atmosphere through valve body 28 and permit an uninterrupted exhaust gas flow through the valve device to atmosphere.

During normal operation of the pressure generating device 12, gas flows from the pressure generating device 12 through the delivery conduit 14 and into the interior of patient interface 20. When the pressure generating device 12 is generating a flow of gas at a level suitable for treatment of the patient, the pressure of the gas within the patient interface will be sufficient to overcome the force of gravity acting on the weight of ball 36. As a result, ball 36 moves to a "closed" or "exhaust"

position, in which the ball is disposed at or near outlet 34 of interior chamber 30, as shown by position A in FIG. 4. When in this position, ribs 38 provide a gap between the ball and the sidewall of the valve body such that exhaust gas is permitted to flow around the ball and out outlet 34 of the body. In other words, when ball 36 is in the "closed" position, the flow of exhaust gas flow through valve device 22 to the atmosphere is restricted, but is not completely shut off. In the exhaust position, the valve device provides an outlet for the removal of gas from the system to the ambient atmosphere during exhalation much like a conventional exhaust port. It can be appreciated that the size of the gap between the ball and the sidewall, which is defined by the height of the ribs, determines the flow rate of the exhaust gas.

When the flow of gas is decreased or interrupted or when the pressure drops below a certain level, ball 36 will fall to the "entrainment valve" or "open" position, in which the ball is resting on the retaining seat (position B in FIG. 4). This allows a maximum flow of gas around ball 36 and through valve device 22. Gas is not only able to leave the patient interface through valve device 22 when the ball is in the open position B, but fresh air is also able to flow through the valve device from the atmosphere into the patient interface and to the airway of a patient.

It can be appreciated that because gravity is the biasing force that urges the ball into the "open" position, the operation of the valve device will be position dependent. Therefore, the present invention contemplates providing multiple valve devices 22 positioned strategically on the patient interface faceplate to provide a sufficient level of venting regardless of the position of the patient interface.

Figure 6:
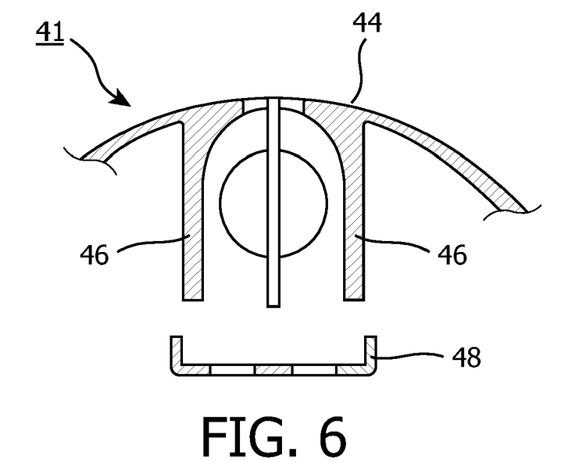
FIG. 6 is a sectional, cut-away, exploded view of a second embodiment of a valve device according to the principles of the present invention.
Figure 7:
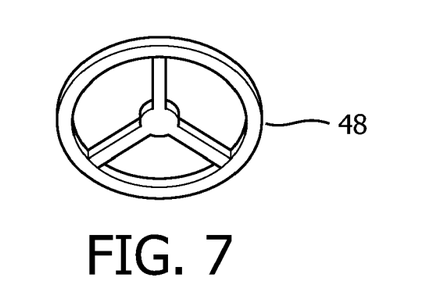
FIG. 7 is a top view of a retaining member in the valve device of FIG. 6.

A second embodiment of a valve device 41, which is also gravity based, is illustrated in FIGS. 6 and 7. In this embodiment, valve device 41 includes a valve body 44 that is not formed from a continuous surface, as in the embodiment of FIGS. 3-5, but is formed from evenly spaced protrusions or ribs 46. A retaining member 48 is spaced below ribs 46 to prevent ball 36 from escaping the cavity formed by the ribs. This embodiment allows the entire valve device to remain below the surface of the faceplate so that there are no protrusions from the exposed exterior surface of the faceplate. Of course, the present invention also contemplates that the conical valve body in the first embodiment can be recessed into the faceplate so that no protrusions are present in that embodiment either. Eliminating the protrusions from the faceplate is believed to provide a more aesthetically pleasing interface device.

Figure 8:
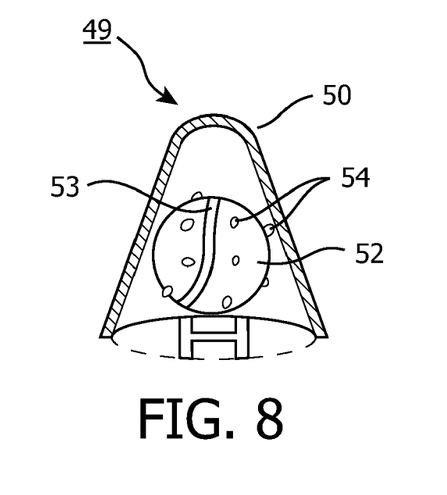
FIG. 8 is side sectional view of a third embodiment of a valve device according to the principles of a the present invention.

A third embodiment of a valve device 49, which is also gravity based, is shown in FIG. 8. In this embodiment, the ribs are omitted from sidewall 50, so that the sidewalls of the interior chamber are smooth. The valve element is again a ball 52. However, ball 52 includes protrusions or bumps 54 to prevent the valve device from completely blocking the flow of exhaust gas through the valve body when the valve element is in the "closed" position. Bumps 54 comprise a valve structure preventing the ball from completely blocking the valve device from the atmosphere, while permitting a flow of exhaust gas through the valve device and the atmosphere. The present invention also contemplates that grooves 53 can be provided in the ball 52, in addition to, or in place of, the bumps 54, so that exhaust gas can flow around the ball 52 through the groove 53. The height of the bumps define the flow rate through the valve device when in the "closed" position. It should also be understood that the present invention contemplates providing dimples, recesses, grooves, or a similar structure in the ball device to provide the path for gas to flow when the valve device is in the "closed" position. In addition, the valve element need not be a ball, but can have any configuration that accomplishes the function of the valve element discussed herein.

Figure 9:
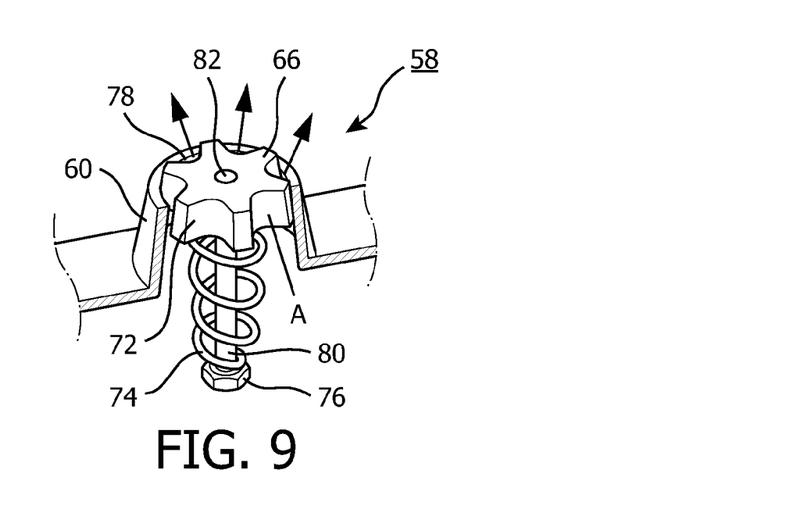
FIG. 9 is partially sectional side view of a fourth embodiment of a valve device according to the principles of the present invention.
Figure 10:
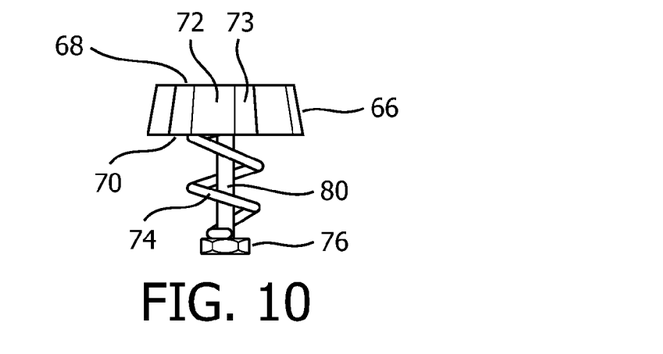
FIG. 10 is a side view of the valve plug and spring in the valve device of FIG. 9.

A fourth embodiment of a valve device 58 according to the principles of the present invention is shown in FIGS. 9-10. In this embodiment, the biasing force acting on the valve element is a spring rather than gravity. In other words, the biasing that urges the valve element to return the "open" position is a spring force, rather than a gravitational force. In this embodiment, valve device 58 has a frusta-conical shaped valve body 60 that defines a chamber 62 having smooth interior sidewall 64. The valve element in this exemplary embodiment is a frusta-conical shaped plug 66 having a first side 68, a second side 70, and a plurality of radially spaced grooves 72 disposed about its perimeter. Grooves 72 extend from the first side to the second side. It should be noted that plug 66 could also be described has having a plurality of protrusions 73 disposed around it perimeter with a gap 72 between each protrusion. A spring 74 is attached to second side 70 of plug 66 and to a retaining member 76, which is attached to the patient interface faceplate. Although the attachment of retaining member 76 to the faceplate is not shown in these figures, the present invention contemplates coupling the retaining member to the faceplate using any suitable technique.

Figure 11:
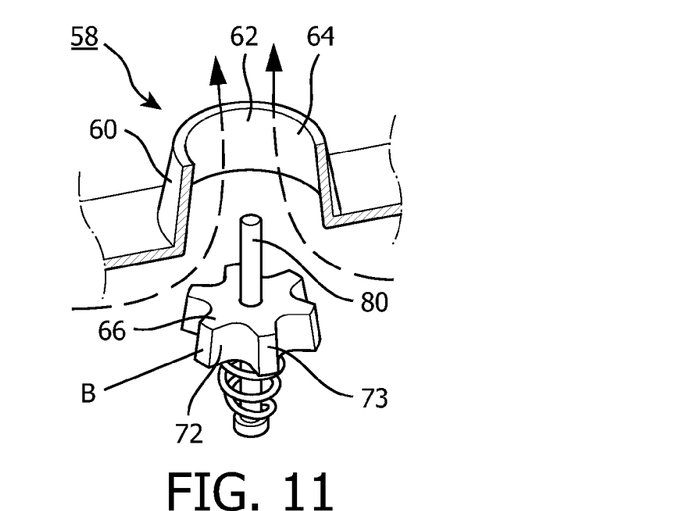
FIG. 11 is a sectional view of the valve device FIG. 9 shown in an "open" position.

When operating under pressure, plug 66 will operate against the force of spring 74 and move to a "closed" position (position A in FIG. 9). When in the "closed" position A, exhaust gas is permitted to pass through the gaps defined by grooves 72 and sidewall 64 of interior chamber 62 and exit from the valve device at outlet 78 of valve body 60. Grooves 72 (or protrusions 73) form a valve structure that prevents the plug from completely blocking the valve device, i.e., from completely restricting the flow of exhaust gas to the atmosphere, while permitting the flow of exhaust gas through the valve device to the atmosphere. When operating under no, decreased, or insufficient pressure or flow, the plug will stay in a lowermost or "open" position (position B in FIG. 11), where the plug is offset or below valve body 60, thereby allowing a maximum flow of gas around the plug and through valve device 58. The minimum pressure required to advance plug 66 to the exhaust valve position A is preferably set at 2 to 3 cm $H_2O$ and is controlled by the force of spring 74. Therefore, when the pressure drops below the minimum pressure, valve device 58 will open.

The present invention contemplates that valve device 58 includes a guiding system, which comprises a guide member 80 attached to retaining member 76. Guide member 80 is received in a through hole 82 provided through the center of plug 66 so that the plug slides along the guide member. This ensures that the plug is properly aligned within the valve body.

Preferably plug 66 is molded in one piece. Also, the plug is preferably made out of a soft (elastic) material, such as silicone or other elastomeric material. The use of an elastic plug ensures a good seal with the valve body when in the "closed" position, so that the exhaust flow is well regulated. It should also be noted that the wall of the valve device can also been made from an elastic or elastomeric material or both the plug and wall can be made from an elastomeric material. Such material is believed to be beneficiation in that it will absorb or minimize noise during exhausting of gas through soft openings. The present invention also contemplates that the plug and spring are made from a common elastic material, there by simplifying the number of components and the assembly process for the valve device. The valve device may be incorporated on patient interface 20, may be positioned at any point between pressure generating device 12 and the patient interface 20, or at both locations.

Figure 12:
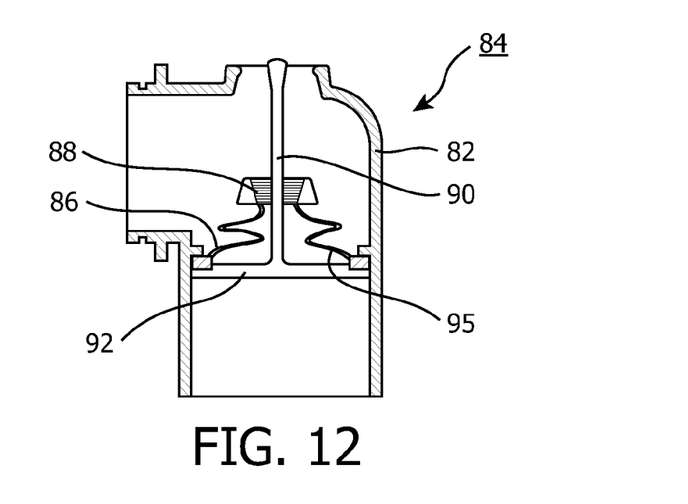
FIG. 12 is a side sectional view of a portion of a patient circuit including a fifth embodiment of a valve device according to the present invention and shown in an "open" position.
Figure 13:
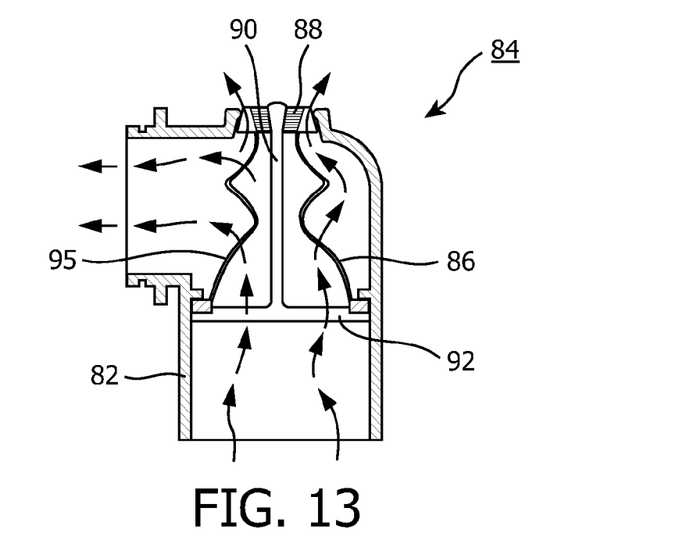
FIG. 13 is a side sectional view of the valve device of FIG. 12 shown in a "closed" position"
Figure 14:
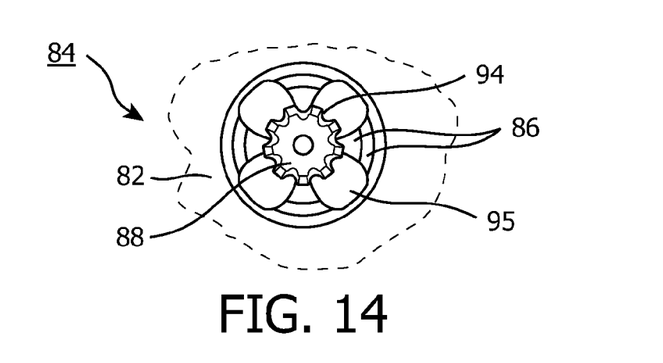
FIG. 14 is a top view of the valve device of FIG. 12.
Figure 15:
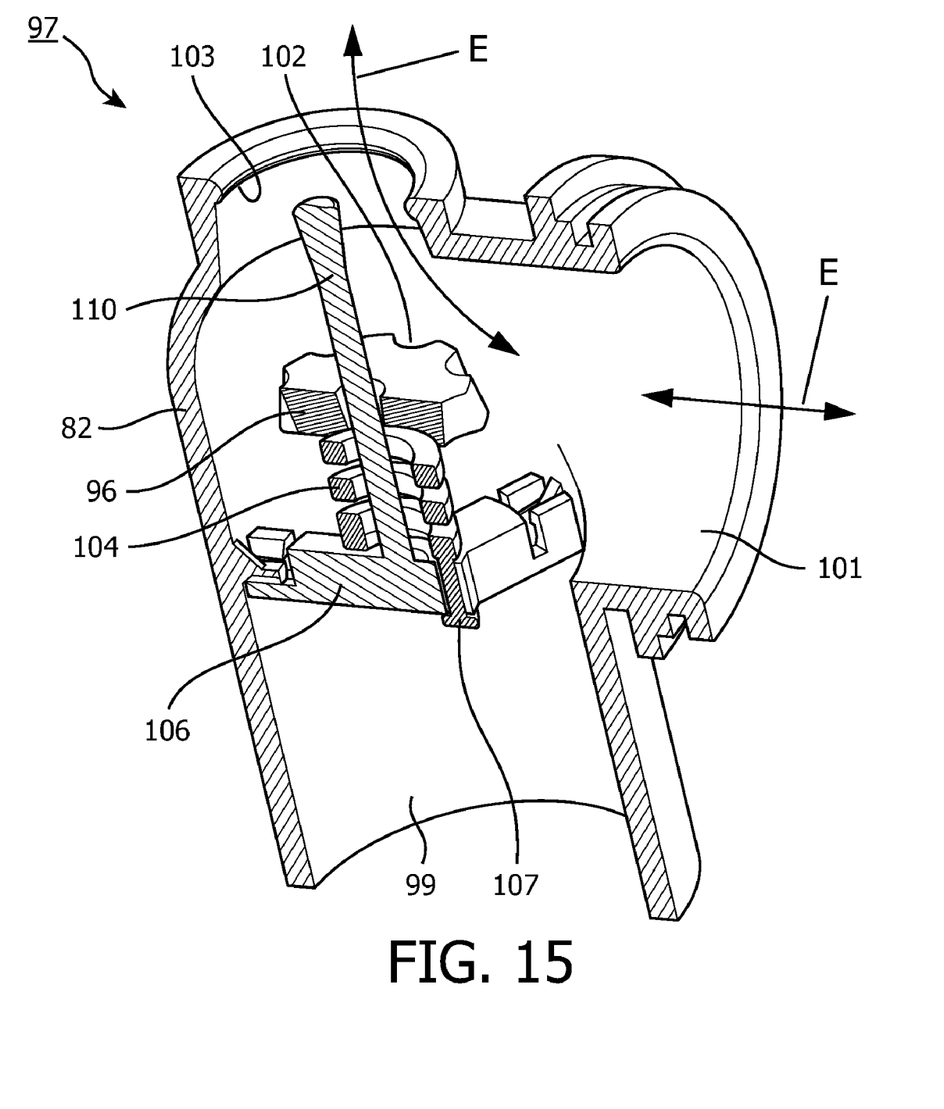
FIG. 15 is a perspective sectional view of sixth embodiment of a valve device according to the principles of the present invention.

A fifth embodiment of a valve device 84 according to the present invention is shown in FIGS. 12-14. FIG. 12 shows a valve element in a "open" position, and FIG. 13 shown the valve element in an "closed" position. In this exemplary embodiment, valve device 84 is provided in an elbow coupling 82, which typically attaches a patient circuit to a patient interface device. For present purposes, the elbow coupling can be considered as part of the patient interface or as part of the patient circuit.

Valve device 84 includes an extendable diaphragm 86 disposed within the elbow coupling 82. Valve device 84 includes a valve element in the form of a plug 88 that is moveable between an open position (FIG. 12) and a closed position (FIG. 13). Plug 88 extends to the closed position as a result of the pressure and/or the flow pushing on a surface of diaphragm 86. A guide member 90 extends from a retaining member 92. The plug includes side openings 94, which allow gas to escape around the plug when in the closed or exhaust position. At least one opening 95 is defined in diaphragm 86 to allow gas to flow from one end of the elbow coupling to the other.

FIGS. 15-19 illustrate a sixth embodiment of a valve device 97 according to the principles of the present invention. In this embodiment, valve device 97 is a spring-loaded valve that is disposed in a patient interface elbow 82. Elbow 82 includes a first end portion 99 that attaches to a patient circuit and a second end portion 101 that attached to a patient interface. An opening 103 is defined through the elbow wall between the first and second end portions. Preferably, opening 103 is situated such that gas exiting the opening is not directed onto the user.

Figure 16:
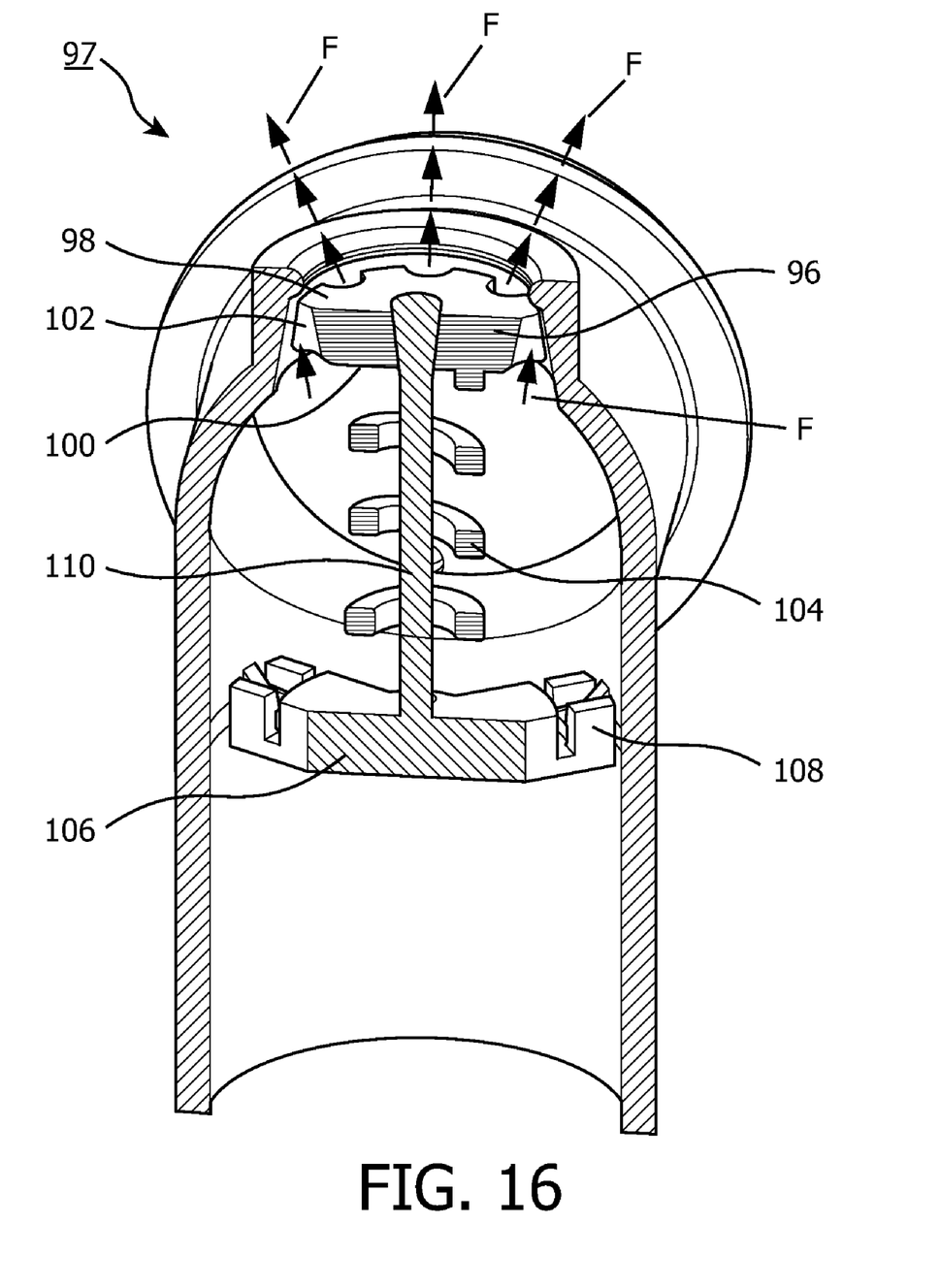
FIGS. 16 and 17 are sectional views of the valve device of FIG. 15 shown in a "closed" position and an "open" position, respectively.
Figure 17:
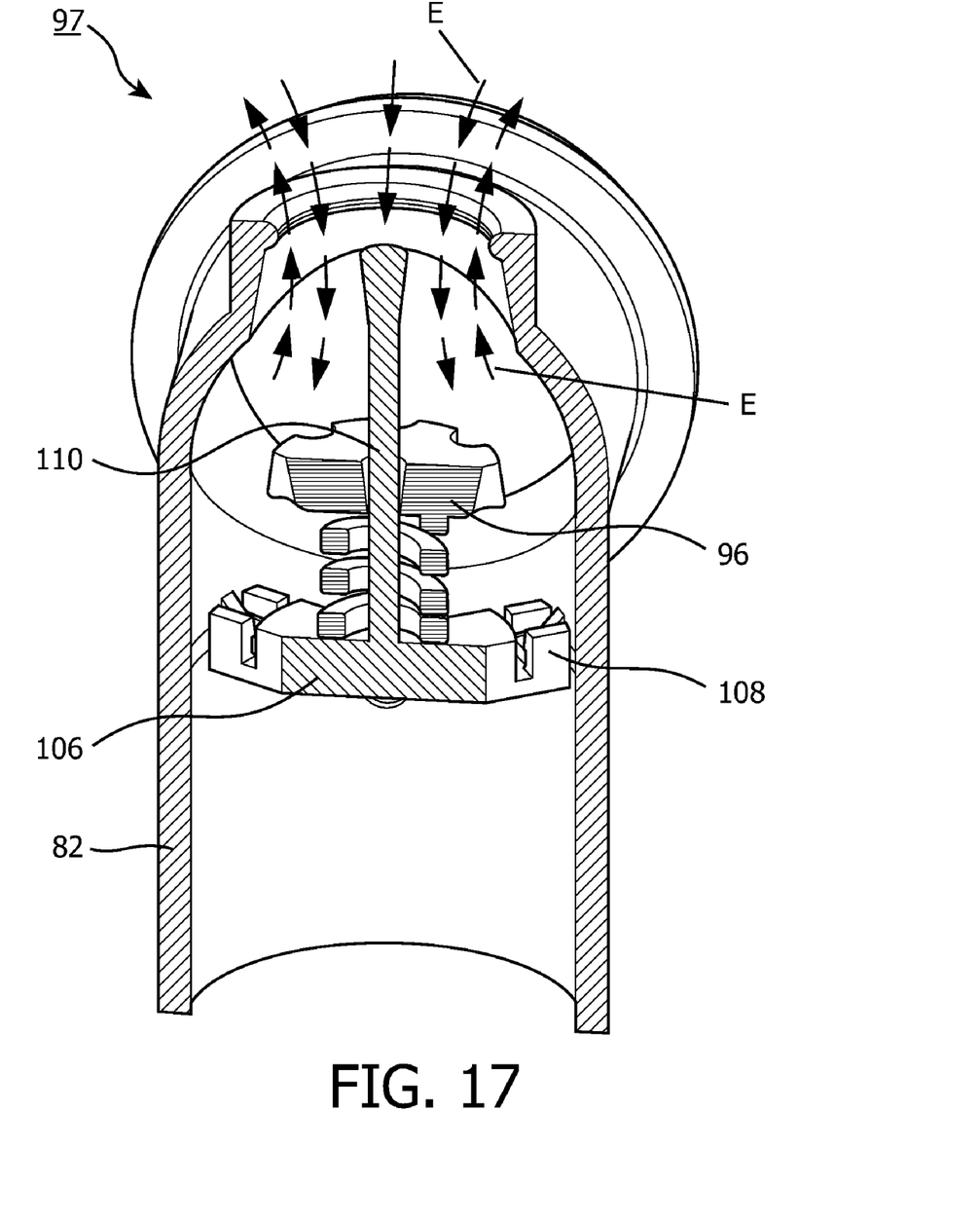
Figure 18:
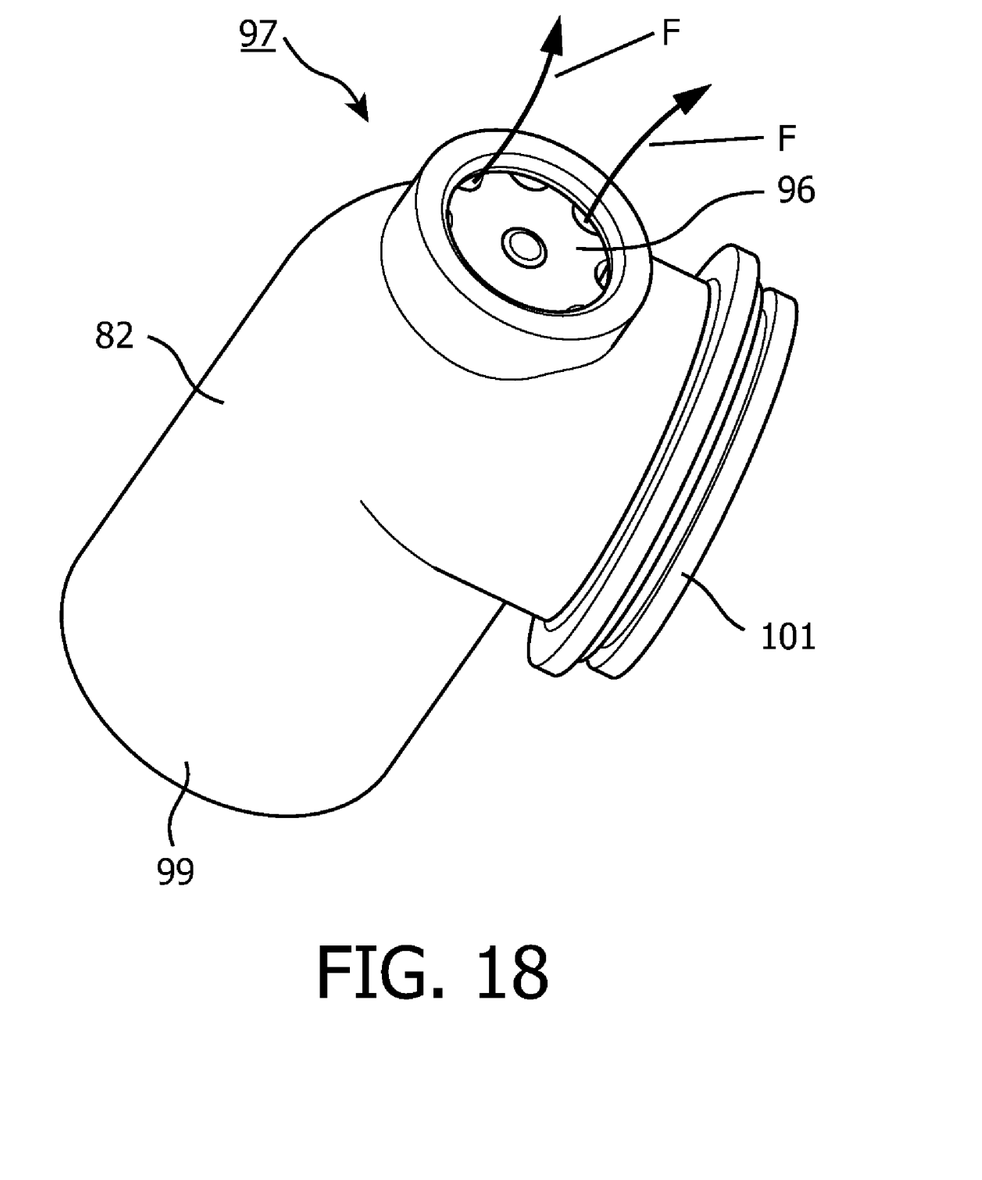
FIG. 18 is a perspective view of the valve device of FIG. 15.
Figure 19:
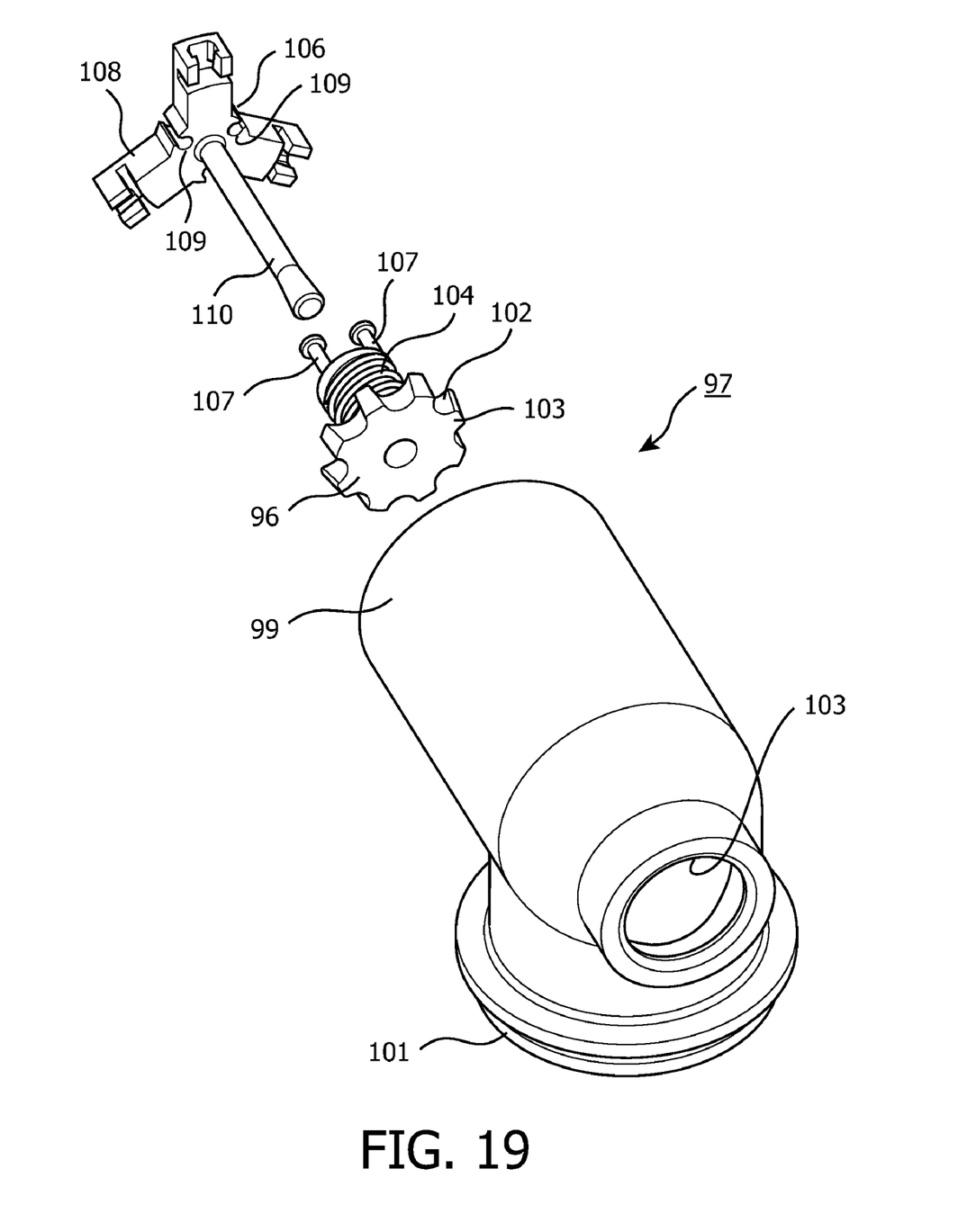
FIG. 19 is an exploded view of the valve device of FIG. 15.

Valve device 97 includes a plug 96 that is moveable between an "open" position (FIGS. 15 and 17) and a "closed" position (FIGS. 16 and 18). Plug 96 has a first side 98, a second side 100 and a plurality of radially spaced grooves 102 disposed about its perimeter. Grooves 102 extend from the first side to the second side. It should be noted that plug 96 could also be described has having a plurality of protrusions 103 disposed around it perimeter with a gap 102 between each protrusion. A spring 104 is attached to second side 100 of plug 96 and to a retaining member 106. Although the present invention contemplates that spring 104 can be attached to retaining member 106 in any conventional manner, in the illustrated embodiment, a mechanical coupling is provided by inserting coupling elements 107 into receiving slots 109. The retaining member is attached to the interior of the elbow. Retaining member 106 includes radially spaced bars 108 that attached to elbow 82 and a guide member 110 that extends coaxially with respect to opening 103. Plug 96 is slideable over guide member 110 and is operable as discussed above in the previous embodiments.

More specifically, valve element formed by plug 96 is coupled to a valve body in the form of elbow 82 such that the valve element is moveable between at least two positions. These positions include a first (open) position, as shown in FIG. 17, in which an exhaust gas flow between the valve device and an ambient atmosphere, indicated by arrows E, is at first level of restriction. Plug 96 is maintained in this position due to flow of gas in the elbow having an insufficient pressure or rate of flow to overcome a biasing force acting on plug 96 provided by spring 104 that otherwise urges plug 96 toward retaining remember 106 and out of opening 103. In this first position, the user's airway is open to the ambient atmosphere, as indicated by arrows E in FIGS. 15 and 17.

A second (closed) position for plug 96 is shown in FIGS. 16 and 18. In this position, the gas flow shown by arrows F is at a second level of restriction that is greater than the first level of restriction. As a result, gas flow F is perhaps better referred to as a gas exchange, with fresh air entering the system and exhaled CO2 exiting, than an exhaust flow, because of the decreased level of restriction provided be moving the plug to the open position. Plug 96 is maintained in this second position due to flow of gas in the elbow having a sufficient pressure or rate of flow to overcome a biasing force acting on plug 96 provided by spring 104 that otherwise urges plug 96 toward retaining remember 106 and out of opening 103. In this first position, the valve device provides a flow restriction commensurate with that provided by a conventional exhaust port, i.e., sufficient to allow gas to wash out of the system, but great enough to maintain a pressure within the system so that the user receives the benefits of the pressure support therapy provided by the pressure/flow generating system.

While FIGS. 15-19 illustrate valve device 97 as being provided on an elbow portion of a patient circuit or patient interface, it is to be understood that the valve device can be provided on other components of the system, such as in the patient interface (including the faceplate, the seal, or both) or at other locations along the patient circuit. In addition, elbow 82 need not be a 90° elbow, but can have any angle from 0-180 degrees. Of course, at a zero degree angle, the elbow is effectively a portion of the patient circuit or patient interface and is not an elbow.

In the embodiments illustrated above, the valve device is either gravity or spring driven. In other words, the biasing force acting on the valve element to return the valve element to the "open" position in these embodiments is either a gravitational force on the weight of the valve element or a spring force acting on the valve element. It is to be understood that the present invention contemplates that the biasing force may be any type of force suitable for returning the valve element to the open position should gas pressure be interrupted or diminished. The valve element will thus, return to the open position when the pressurized gas delivered by the pressure generating device is insufficient to overcome the biasing force. An example of an alternate biasing force is magnetic (either actively or passively). In an active application, a magnet is disposed to draw a ferro-magnetic ball to the "open" position. In a passive application, an electrically induced magnetic force moves the valve to the "exhaust" valve position. In the case of an interruption of power, the magnetic force diminishes, therefore, the valve will return to the "open" position.

Based on the foregoing description and the illustrations, it can be appreciated that the present invention provides a pressure sensitive valve device adapted for use with respiratory equipment of the type that produces a pressurized flow of breathing gas. The valve device combines the exhalation and entrainment functions in one valve with a single air path. The valve device provides both an exhaust valve function during normal operation and provides access to the ambient atmosphere in the event of respiratory equipment malfunction.

During normal operation when the pressure generating device is generating a flow of gas, the valve element will be positioned in an "closed" valve position. When the valve element is in the exhaust position, the gas flow from the valve device to the atmosphere is restricted without being completely blocked off. A valve structure prevents the valve element from completely blocking the valve device from the atmosphere, and continuously permits gas flow between the valve device and the atmosphere. In the closed position, the valve device provides an outlet for the removal of gas upon expiration.

When the flow of gas is decreased or interrupted or when the pressure drops below a certain level, the valve element will fall to the "entrainment valve" or "open" position, wherein the valve element is in a position remote from the gas outlet allowing a maximum, e.g., and unrestricted, flow of gas around the valve element and through the valve device. Gas is not only able to leave the patient interface through the valve device in the open position, but fresh air is also able to flow through the valve device from the atmosphere into the patient interface to the patient. The valve device of the present invention is compact and can be incorporated on the patient interface or as an in-line attachment to the mask elbow.

An additional advantage of the present invention is the valve device has variable openings, one opening for the exhalation function and one opening for the entrainment function. The valve changes from one opening to the other triggered by the pressure level or the rate of flow of gas in the system. The valve element controls the degree of opening of the valve device in order to control the amount of gas venting through the valve device. Typically, exhalation valves or exhaust valves have fixed openings, either in the form of holes or slits provided in the valve element, the valve body, or both.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that, to the extent possible, the present invention contemplates that one or more features of any embodiment of the present invention can be combined with the features of any other embodiment.

What is claimed is:

1. A valve device for use in a system for delivering a flow of gas to an airway of a patient, the valve device comprising:
    a valve body having an outlet open to ambient atmosphere;
    a valve element comprising a ball or a plug disposed in the valve body such that the valve element is moveable between at least two positions including a first position, wherein an exhaust gas flow that passes through the outlet between the valve device and an ambient atmosphere is at a first level of restriction, and a second position, wherein the exhaust gas flow that passes through the outlet is at a second level of restriction that is greater than the first level of restriction, such that a flow rate of the exhaust gas flow when the valve element is in the first position is greater than the flow rate of the exhaust gas flow when the valve element is in the second position, wherein the valve element is disposed in the first position responsive to the flow of gas having an insufficient pressure or rate of flow to overcome a biasing force acting on the valve element, and wherein the valve element is disposed in the second position responsive to the flow of gas having a sufficient pressure or rate of flow to overcome the biasing force acting on the valve element; and
    a valve structure adapted to prevent the valve element from completely blocking the exhaust gas flow from passing through the outlet regardless of the position of the valve element relative to the valve body, wherein the valve device is constructed and arranged such that when the valve element is in the first position gas is able to flow from the ambient atmosphere to the airway of the patient through the valve body and gas is able to leave a patient interface and flow into the ambient atmosphere through the valve body, and when the valve element is in the second position the flow of gas generated by the system is at a level suitable for treatment of the patient.

2. The valve device of claim 1, wherein the valve structure comprises:
    (a) a groove defined in the ball or plug; or
    (b) a protrusion disposed on the ball or plug; or both
    (c) the groove and the protrusion.

3. The valve device of claim 1, wherein the biasing force is gravity or a spring.

4. The valve device of claim 1, wherein the valve body further includes an interior chamber having a sidewall, wherein the valve structure is a protrusion on the sidewall.

5. The valve device of claim 1, wherein the valve body is arranged on the patient interface.

6. The valve device of claim 1, wherein the valve structure comprises one or more protrusions arranged on the valve body, or the valve element, or both, the one or more protrusions of the valve structure being adapted to prevent the valve element from completely blocking the exhaust gas flow from passing through the outlet regardless of the position of the valve element relative to the valve body.

7. The valve device of claim 1, wherein when the valve element is in the first position, gas is able to flow to the airway of the patient substantially unobstructed so as to provide a sufficient flow to prevent asphyxiation of the patient.

8. A system for delivering a breathing gas to a patient comprising:
    (a) a gas flow/pressure generating device that produces a flow of gas;
    (b) a conduit having a first end portion operatively coupled to the gas flow generating device and a second end portion, wherein the conduit carries the flow of gas from the gas flow/pressure generating device during operation of the system;
    (c) a patient interface coupled to the second end portion of the conduit; and
    (d) a valve device positioned between a patient and the gas flow generator comprising:
        (1) a valve body having an outlet open to the atmosphere,
        (2) a valve element comprising a ball or a plug disposed in the valve body such that the valve element is moveable between at least two positions including a first position, wherein an exhaust gas flow that passes through the outlet between the valve device and an ambient atmosphere is at first level of restriction, and a second position, wherein the exhaust gas flow that passes through the outlet is at a second level of restriction that is greater than the first level of restriction, such that a flow rate of the exhaust gas flow when the valve element is in the first position is greater than the flow rate of the exhaust gas flow when the valve element is in the second position, wherein the valve element is disposed in the first position responsive to the flow of gas having an insufficient pressure or rate of flow to overcome a biasing force acting on the valve element, and wherein the valve element is disposed in the second position responsive to the flow of gas having a sufficient pressure or rate of flow to overcome the biasing force acting on the valve element, and
        (3) a valve structure adapted to prevent the valve element from completely blocking the exhaust gas flow from passing through the outlet regardless of the position of the valve element relative to the valve body, wherein the valve device is constructed and arranged such that when the valve element is in the first position gas is able to flow from the ambient atmosphere to the airway of the patient through the valve body and gas is able to leave the patient interface and flow into the ambient atmosphere through the valve body, and when the valve element is in the second position the flow of gas generated by the system is at a level suitable for treatment of the patient.

9. The system of claim 8, wherein the valve structure comprises:
(a) a groove defined in the ball or plug; or
(b) a protrusion disposed on the ball or plug; or both
(c) the groove and the protrusion.

10. The system of claim 8, wherein the returning force is gravity or a spring.

11. The system of claim 8, wherein the valve body further includes an interior chamber having a sidewall, wherein the valve structure is a protrusion on the sidewall.

12. The system of claim 8, wherein the valve device is positioned on the patient interface or is disposed between the patient interface and the second end portion of the conduit.

13. The system of claim 12, wherein there are a plurality of valve devices positioned on the patient interface.

14. A patient interface for use in a system for delivering pressurized gas to the airway of a patient, the patient interface comprising:
(a) a faceplate;
(b) a cushion attached to the faceplate; and
(c) a valve device positioned on the faceplate or the cushion, or both, the valve device comprising:
 (1) a valve body having an outlet open to the atmosphere,
 (2) a valve element comprising a ball or a plug disposed in the valve body such that the valve element is moveable between at least two positions including a first position, wherein an exhaust gas flow that passes through the outlet between the valve device and an ambient atmosphere is at first level of restriction, and a second position, wherein the exhaust gas flow that passes through the outlet is at a second level of restriction that is greater than the first level of restriction, such that a flow rate of the exhaust gas flow when the valve element is in the first position is greater than the flow rate of the exhaust gas flow when the valve element is in the second position, wherein the valve element is disposed in the first position responsive to the flow of gas having an insufficient pressure or rate of flow to overcome a biasing force acting on the valve element, and wherein the valve element is disposed in the second position responsive to the flow of gas having a sufficient pressure or rate of flow to overcome the biasing force acting on the valve element, and
 (3) a valve structure adapted to prevent the valve element from completely blocking the exhaust gas flow from passing through the outlet regardless of the position of the valve element relative to the valve body, wherein the valve device is constructed and arranged such that when the valve element is in the first position gas is able to flow from the ambient atmosphere to the airway of the patient through the valve body and gas is able to leave the patient interface and flow into the ambient atmosphere through the valve body, and when the valve element is in the second position the flow of gas generated by the system is at a level suitable for treatment of the patient.

15. The patient interface of claim 14, wherein the valve structure comprises:
(a) a groove defined in the ball or plug; or
(b) a protrusion disposed on the ball or plug; or both
(c) the groove and the protrusion.

16. The patient interface of claim 15, wherein the biasing force is gravity or a spring.

17. The patient interface of claim 14, wherein the valve body further includes an interior chamber having a sidewall, wherein the valve structure is a protrusion on the sidewall.

18. A valve device for use in a system for delivering a flow of gas to an airway of a patient, the valve device comprising:
exhaust flow communicating means for communicating a flow of exhaust gas from such a system to an ambient atmosphere;
restriction controlling means for controlling a level of restriction of the flow of exhaust gas through the exhaust flow communicating means such that a first level of restriction is provided responsive to the flow of gas in the system having a first pressure and a second level of restriction is provided responsive to the flow of gas in the system having a second pressure, the restriction controlling means comprising a ball or a plug disposed in the exhaust flow communicating means, wherein the first level of restriction is less than the second level of restriction and the first pressure is less than the second pressure, such that a flow rate of exhaust gas when the restriction controlling means is in the first level of restriction is greater than the flow rate of the exhaust gas when the restriction controlling means is in the second level of restriction; and
blockage preventing means for preventing the restricting controlling means from completely blocking the exhaust flow communicating means regardless of the position of the restriction controlling means relative to the exhaust flow communicating means, wherein the valve device is constructed and arranged such that when the restriction controlling means is in the first position gas is able to flow from the ambient atmosphere to the airway of the patient through the exhaust flow communicating means and gas is able to leave a patient interface and flow into the ambient atmosphere through the exhaust flow communicating means, and when the restriction controlling means is in the second position the flow of gas generated by the system is at a level suitable for treatment of the patient.

19. The valve device of claim 18, wherein the exhaust flow communicating means comprises a valve body having an outlet open to ambient atmosphere disposed on a component of the system for delivering a flow of gas to an airway of a patient.

20. The valve device of claim 18, wherein the blockage preventing means comprises a groove or protrusion associated with the exhaust flow communicating means, the restriction controlling means, or both.

21. The valve device of claim 18, wherein the exhaust flow communicating means is arranged on the patient interface.

22. A system for delivering a breathing gas to a patient comprising:
(a) gas flow/pressure generating means for producing a flow of gas;
(b) communicating means for carrying the flow of gas to an airway of a patient; and
(c) a valve device operatively coupled to the communicating means, wherein the valve device comprises:
 (1) exhaust flow communicating means for communicating a flow of exhaust gas from such a system to an ambient atmosphere,
 (2) restriction controlling means for controlling a level of restriction of the gas flow of exhaust gas through the exhaust gas flow communicating means such that a first level of restriction is provided responsive to the flow of gas having a first pressure and a second level of restriction is provided responsive to the flow of gas having a second pressure, the restriction controlling means comprising a ball or a plug disposed in the exhaust flow communicating means, wherein the first level of restriction is less that the second level of restriction and the first pressure is less than the second pressure, such that a flow rate of exhaust gas when the restriction controlling means is in the first level of restriction is greater than the flow rate of the exhaust gas when the restriction controlling means is in the second level of restriction; and (3) blockage preventing means for preventing the means for controlling a level of restriction from completely blocking the exhaust flow communicating means regardless of the position of the restriction controlling means relative to the exhaust flow communicating means, wherein the valve device is constructed and arranged such that when the restriction controlling means is in the first position gas is able to flow from the ambient atmosphere to the airway of the patient through the exhaust flow communicating means and gas is able to leave a patient interface and flow into the ambient atmosphere through the exhaust flow communicating means, and when the restriction controlling means is in the second position the flow of gas generated by the gas flow/pressure generating means is at a level suitable for treatment of the patient.

23. The system of claim 22, wherein the exhaust flow communicating means comprises a valve body having an outlet open to ambient atmosphere disposed on a component of the system for delivering a flow of gas to an airway of a patient.

24. The system of claim 22, wherein the blockage preventing means comprises a groove or protrusion associated with the exhaust flow communicating means, the restriction controlling means, or both.

25. The system of claim 22, wherein the exhaust flow communicating means is arranged on the patient interface.

* * * * *